(12) United States Patent
Neumann

(10) Patent No.: US 11,798,652 B2
(45) Date of Patent: Oct. 24, 2023

(54) METHOD OF AND SYSTEM FOR IDENTIFYING AND AMELIORATING BODY DEGRADATIONS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 91 days.

(21) Appl. No.: 17/000,929

(22) Filed: Aug. 24, 2020

(65) Prior Publication Data
US 2022/0059188 A1 Feb. 24, 2022

(51) Int. Cl.
*G16B 40/00* (2019.01)
*G06N 20/00* (2019.01)
(Continued)

(52) U.S. Cl.
CPC .......... *G16B 40/00* (2019.02); *G06F 18/2113* (2023.01); *G06F 18/2115* (2023.01);
(Continued)

(58) Field of Classification Search
CPC ........ G16B 40/00; G16B 25/00; G16B 45/00; G16B 50/00; G06K 9/623; G06K 9/6231;
(Continued)

(56) References Cited

U.S. PATENT DOCUMENTS

| 6,692,916 B2 | 2/2004 | Bevilacqua et al. |
| 7,761,309 B2 | 7/2010 | Sacco et al. |

(Continued)

FOREIGN PATENT DOCUMENTS

CN 110491520 A * 11/2019

OTHER PUBLICATIONS

Translation of the title and abstract for CN-110491520-A (Year: 2019).*
https://diginole.lib.fsu.edu/islandora/object/fsu%3A507684/datastream/PDF/view.

*Primary Examiner* — Jesse P Frumkin
(74) *Attorney, Agent, or Firm* — CALDWELL INTELLECTUAL PROPERTY LAW

(57) ABSTRACT

A system for identifying and ameliorating body degradations, the system comprising a computing device, wherein the computing device is configured to receive biological extraction data. Computing device may generate, as a function of a degradation machine-learning model and the biological extraction data, a degradation profile. Computing device may calculate a biological degradation function that is a mathematical function that describes the change in rate of degradation over time corresponding to the user. Computing device may identify, using a degradation imbalance machine-learning process and the degradation profile, a degradation imbalance. Computing device may determine, as a function of the degradation imbalance machine-learning process and the degradation imbalance, a degradation antidote strategy to decrease the rate of biological degradation of a user by performing a simulation. Computing device may display to a user the degradation antidote strategy and a degradation prevention instruction set for a user to alter degradation rates.

20 Claims, 10 Drawing Sheets

(51) Int. Cl.
*G16B 25/00* (2019.01)
*G16B 50/00* (2019.01)
*G16B 45/00* (2019.01)
*G16H 50/20* (2018.01)
*G16H 50/30* (2018.01)
*G06F 18/2113* (2023.01)
*G06F 18/2115* (2023.01)
*G06F 18/2411* (2023.01)

(52) U.S. Cl.
CPC ......... *G06F 18/2411* (2023.01); *G06N 20/00* (2019.01); *G16B 25/00* (2019.02); *G16B 45/00* (2019.02); *G16B 50/00* (2019.02); *G16H 50/20* (2018.01); *G16H 50/30* (2018.01)

(58) Field of Classification Search
CPC .. G06K 9/6269; G06K 9/6256; G06K 9/6267; G06N 20/00; G16H 50/20; G16H 50/30
See application file for complete search history.

(56) References Cited

U.S. PATENT DOCUMENTS

| | | | |
|---|---|---|---|
| 7,853,626 | B2 | 12/2010 | Jung et al. |
| 7,953,613 | B2 | 5/2011 | Gizewski |
| 8,388,530 | B2 | 3/2013 | Shusterman |
| 9,492,114 | B2 | 11/2016 | Reiman |
| 10,085,643 | B2 | 10/2018 | Bandic et al. |
| 11,416,776 | B2* | 8/2022 | Neumann ............... G06N 20/10 |
| 2011/0208033 | A1* | 8/2011 | Nicolella ............... A61B 5/103 |
| | | | 600/407 |
| 2013/0041683 | A1* | 2/2013 | Boissel .................... G16B 5/00 |
| | | | 705/2 |
| 2018/0039726 | A1* | 2/2018 | Boissel .................... G16B 5/00 |
| 2018/0247020 | A1* | 8/2018 | Itu ........................... G16H 10/60 |
| 2018/0284141 | A1 | 10/2018 | Ayton et al. |
| 2019/0027249 | A1 | 1/2019 | Fuksenko et al. |
| 2021/0212647 | A1* | 7/2021 | Zheng .................. G06K 9/6272 |
| 2022/0058520 | A1* | 2/2022 | Neumann ............... G06N 7/005 |

\* cited by examiner

METHOD OF AND SYSTEM FOR IDENTIFYING AND AMELIORATING BODY DEGRADATIONS

FIELD OF THE INVENTION

The present invention generally relates to the field of machine-learning. In particular, the present invention is directed to a method of and system for identifying and ameliorating body degradations.

BACKGROUND

Efficient systems for tracking age-related biological degradations suffer from difficulties in adequately sampling the breadth of physiological parameters that relate to degradation over the lifetime of the user. Furthermore, systems encounter difficulty in efficiently and properly identifying the ways in which degradations occur, capturing the amounts of degradation and rates of degradation, and predicting degradation trajectories from these confounding variables.

SUMMARY OF THE DISCLOSURE

In an aspect, a system for identifying and ameliorating body degradations includes a computing device, wherein the computing device is designed and configured to receive a biological extraction datum pertaining to a user, generate, as a function of a degradation machine-learning model and the biological extraction datum, a degradation profile, wherein generating the degradation profile further comprises training the degradation machine-learning model using training data that corresponds to biological extraction data correlated to a threshold value of biological degradation, and calculating a biological degradation function of a user that is a mathematical function that describes the change in rate of degradation over time corresponding to the degradation data, identify, using a degradation imbalance machine-learning process and the degradation profile, a degradation imbalance, wherein a degradation imbalance is a rate of biological degradation that exceeds the expected rate of degradation of a threshold value, determine, as a function of the degradation imbalance machine-learning process and the degradation imbalance, a degradation antidote strategy to decrease the rate of biological degradation of a user, wherein determining a degradation antidote strategy further comprises performing a simulation, wherein the simulation randomly perturbs a parameter, wherein a parameter is an element of numerical data relating to the at least a user biological extraction datum, determining which parameters result in the largest decrease in degradation rate, and matching the parameter that result in the largest decrease in degradation rate with a concomitant change in user biological extraction data, and display to a user, using the degradation antidote strategy and the degradation machine-learning process, a degradation prevention instruction set, wherein the instruction set is a logical order of steps for a user to change in user biological extraction data decrease according to the simulation.

In another aspect, a method for identifying and ameliorating body degradations includes a computing device, wherein the computing device is designed and configured to receive a biological extraction datum pertaining to a user, generate, as a function of a degradation machine-learning model and the biological extraction datum, a degradation profile, wherein generating the degradation profile further comprises training the degradation machine-learning model using training data that corresponds to biological extraction data correlated to a threshold value of biological degradation, and calculating a biological degradation function of a user that is a mathematical function that describes the change in rate of degradation over time corresponding to the degradation data, identify, using a degradation imbalance machine-learning process and the degradation profile, a degradation imbalance, wherein a degradation imbalance is a rate of biological degradation that exceeds the expected rate of degradation of a threshold value, determine, as a function of the degradation imbalance machine-learning process and the degradation imbalance, a degradation antidote strategy to decrease the rate of biological degradation of a user, wherein determining a degradation antidote strategy further comprises performing a simulation, wherein the simulation randomly perturbs a parameter, wherein a parameter is an element of numerical data relating to the at least a user biological extraction datum, determining which parameters result in the largest decrease in degradation rate, and matching the parameter that result in the largest decrease in degradation rate with a concomitant change in user biological extraction data, and display to a user, using the degradation antidote strategy and the degradation machine-learning process, a degradation prevention instruction set, wherein the instruction set is a logical order of steps for a user to change in user biological extraction data decrease according to the simulation.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for identifying and ameliorating body degradation. In an embodiment, a computing device may receive biological extraction data from a user and determine rates of biological degradation. Computing device may train a machine-learning model to accurately determine the rates at which a user's body is undergoing biological and physiological degradation in a variety of categories. Computing device may perform computational simulations using a machine-learning process to randomly perturb biological extraction data parameters to simulation on a large-scale the rates of biological degradation over the life of a user. Such a machine-learning process may guide the simulation by determining which parameters are decreasing rates of body degradation and relate these decreases in rate to concomitant changes in user data parameters. In an embodiment, these changes in biological degradation rates may relate to actionable changes in user lifestyle that can be provided to a user as instructions to ameliorate degradation rates and prevent future degradation.

Figure 1:
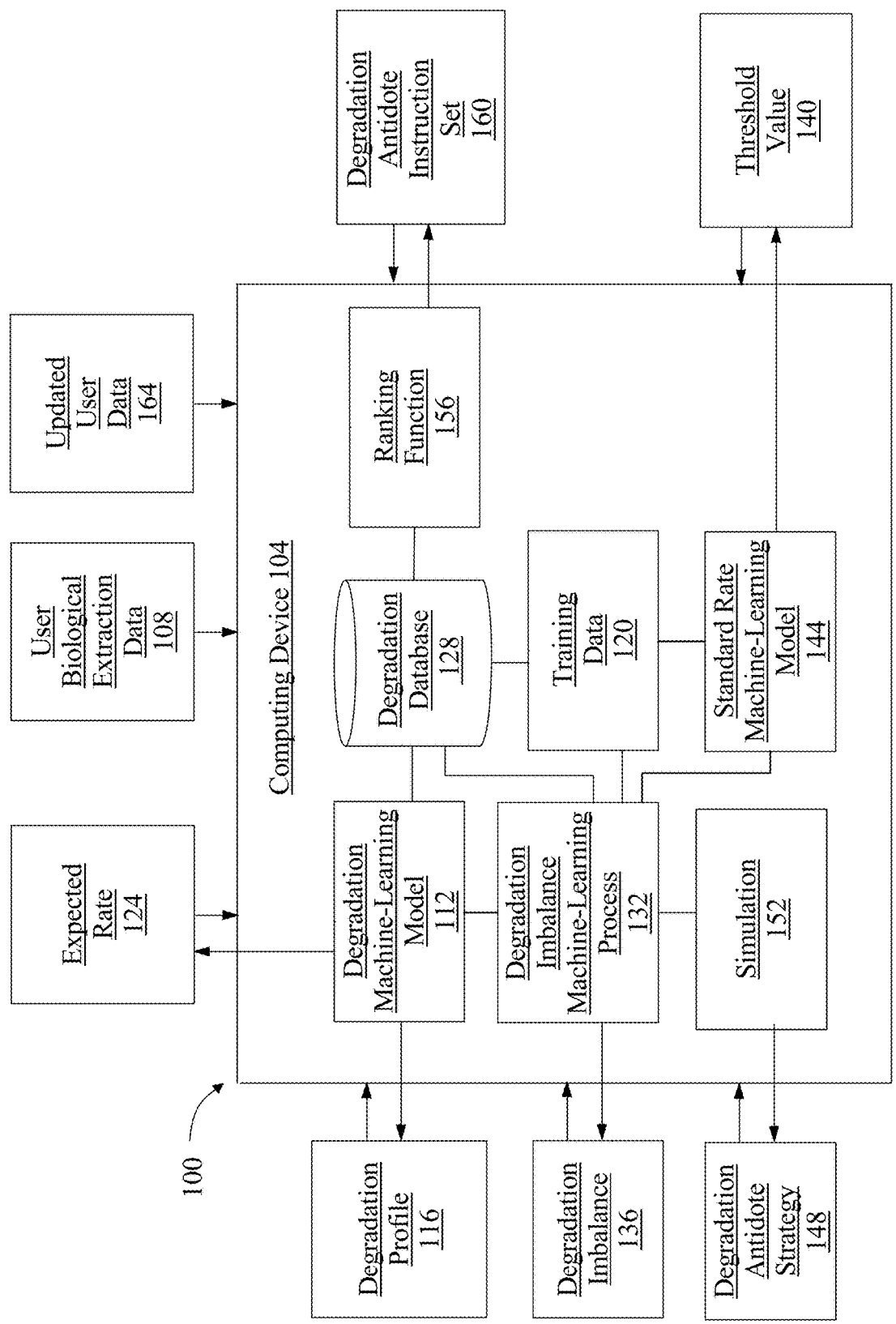
FIG. 1 is a block diagram illustrating a non-limiting exemplary embodiment of a system of identifying and ameliorating body degradations.

Referring now to FIG. 1, an exemplary embodiment of a system 100 for identifying and ameliorating body degradation is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 may receive a biological extraction datum 108 pertaining to a user. A "biological extraction datum," as used in this disclosure refers to a least an element of biological extraction data, wherein biological extraction data refers to any biomarker, genetic data or epigenetic indication, microbiome, or any chemical, biological, or physiological markers of data of a user, including for instance, and without limitation, as described in U.S. Nonprovisional application Ser. No. 16/885,647, filed on Jul. 22, 2020, and entitled "METHODS AND SYSTEMS FOR DETERMINING A PLURALITY OF DIMENSIONS OF BIOLOGICAL EXTRACTION USER DATA AND ARTIFICIAL INTELLIGENCE," the entirety of which is incorporated herein by reference. Biological extraction datum 108 may originate from a wearable device, such as a pacemaker, gyrometer, accelerometer, bioimpedance monitor, pedometer, or any other wearable device and/or medical device. Biological extraction datum 108 may originate from a user questionnaire or any other source wherein the user provides information via an interface, wherein the information is a determination made by a user. User biological extraction datum 108 may origination from a medical professional, physician, caretaker, or the like, on behalf of a user. Computing device 104 may receive at least a biological extraction datum 108 by retrieval from a database, as described in further detail below. Computing device 104 may receive at least a biological extraction datum 108 via a user, wearable device, and/or secondary individual, via a graphical user interface (GUI), web-based platform, application, or the like. Persons skilled in the art, upon reviewing the entirety of this disclosure, will be aware of various ways in which biological extraction data may be received by a computing device for the purposes herein.

Continuing in reference to FIG. 1, computing device 104 may generate, using a degradation machine-learning model 112 and the biological extraction datum 108, a degradation profile 116, wherein generating the degradation profile 116 may include training the degradation machine-learning model 112 using training data 120 that correlates biological extraction data with biological degradation data. A "degradation profile," as used in this disclosure, refers to at least a current level of biological degradation and at least a rate of biological degradation, wherein the degradation level is a relative level of physiological integrity compared to theoretical level of physiological integrity according to what is scientifically achievable for an individual. A "degradation rate" as used in this disclosure refers to the level of degradation changing over time, as an individual ages; degradation rate may be an instantaneous rate or a value of rate that is over a different range of time. As used in this disclosure, "biological degradation" refers to a loss of physiological integrity of biological parameters. Biological degradation may include physiological deterioration of, for instance and without limitation, vision, hearing, cardiovascular endurance, short-term memory, mental plasticity, and the like.

With continued reference to FIG. 1, in non-limiting illustrative examples, degradation machine-learning model 112 may train using training data 120 corresponding to at least an element of biological extraction data to determine a user's current physiological integrity of, for instance and without limitation bone density, wherein the degradation machine-learning model 112 can determine the current level of a user's bone density from for instance a dual-energy X-ray absorptiometry (DEXA) scanning, and determine for the user's age, height, sex, fitness level, among other data, the user's current rate of bone density and at what level bone density may be degrading. In such an example, the rate of degradation of bone density could be no change, an increase, or a decrease in bone density from year-to-year. Such a change in bone density may perhaps be a degradation in bone density of an amount that may be described, reflected, summarized, or otherwise communicated numerically as determined by the model trained with user data and bone density data retrieved from, for instance, a database. In non-limiting illustrative examples, a degradation profile 116 for such a user may illustrate that a user current bone density level and the instantaneous rate and projected rate at which the bone density appears to change as the user ages.

Continuing in reference to FIG. 1, computing device 104 generating the degradation profile 116 may include determining an expected rate 124 of biological degradation using data retrieved from a degradation database 128 and a degradation imbalance machine-learning process 132, wherein the degradation machine-learning process 132 may train a degradation machine-learning model 112 with training data 120 corresponding to rates of biological degradation that were retrieved from the degradation database 128. An "expected rate," as used herein, refers to an expected integrity level, expected rate of change, and expected integrity function for a user according to a degradation machine-learning model 112 trained with training data 120 that determines what the 'percent integrity' of a user's physiology and rate of biological degradation that is theoretically expected if there is no change in user lifestyle, actions, physiology as represented in the biological extraction data, and the like; expected rate may include 'expected values' determined from an expected rate. In further non-limiting illustrative examples, the 'expected rate' for bone density may be the expected rate of bone density deterioration, degradation, and/or change of rate, that would be expected an individual that most closely matches the user's sex, age, height, fitness level, medical history, among other biological extraction parameters; otherwise an expected rate of bone density level over time and the associated rate of degradation. A machine-learning model, such as a degradation machine-learning model 112, may be trained using training data 120 by a machine-learning module, including using a machine-learning process, as described in further detail below.

Figure 2:
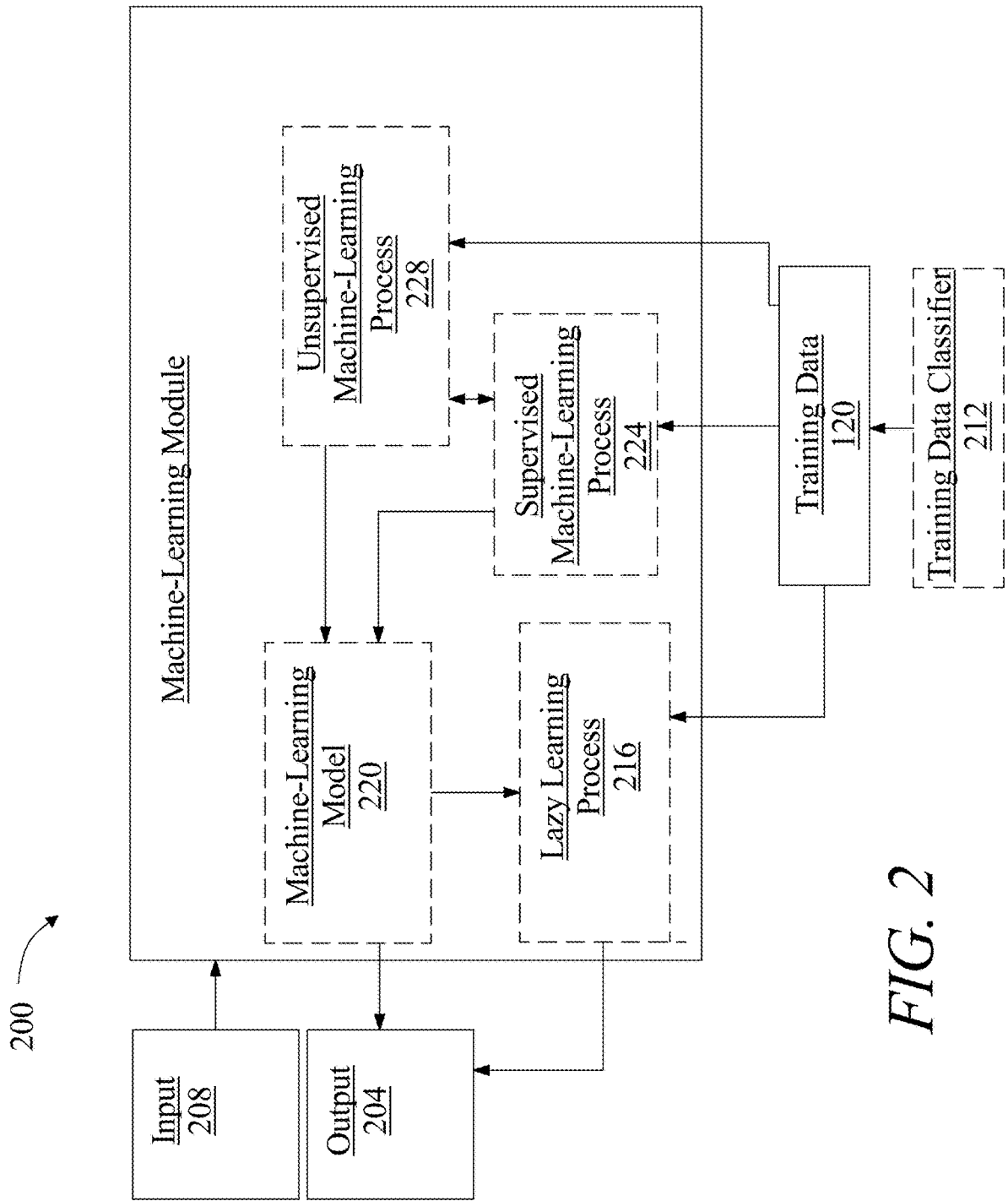
FIG. 2 is a block diagram illustrating a non-limiting exemplary embodiment of a machine-learning module.

Referring now to FIG. 2, an exemplary embodiment of a machine-learning module 200 that may perform one or more machine-learning processes as described in this disclosure is illustrated. Machine-learning module may include any suitable machine-learning module which may perform determinations, classification, and/or analysis steps, methods, processes, or the like as described in this disclosure using machine learning processes. A "machine learning process," as used in this disclosure, is a process that automatedly uses training data 120 to generate an algorithm that will be performed by a computing device/module to produce outputs 204 given data provided as inputs 208; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 120, which may include a plurality of data entries, each entry representing a set of data elements that were recorded, received, and/or generated together; data elements may be correlated by shared existence in a given data entry, by proximity in a given data entry, or the like. Multiple data entries in training data 120 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 120 according to various correlations; correlations may indicate causative and/or predictive links between categories of data elements, which may be modeled as relationships such as mathematical relationships by machine-learning processes as described in further detail below. Training data 120 may be formatted and/or organized by categories of data elements, for instance by associating data elements with one or more descriptors corresponding to categories of data elements. As a non-limiting example, training data 120 may include data entered in standardized forms by persons or processes, such that entry of a given data element in a given field in a form may be mapped to one or more descriptors of categories. Elements in training data 120 may be linked to descriptors of categories by tags, tokens, or other data elements; for instance, and without limitation, training data 120 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 120 may include one or more elements that are not categorized; that is, training data 120 may not be formatted or contain descriptors for some elements of data. Machine-learning algorithms and/or other processes may sort training data 120 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 120 to be made applicable for two or more distinct machine-learning algorithms as described in further detail below. Training data 120 used by machine-learning module 200 may correlate any input data as described in this disclosure to any output data as described in this disclosure. As a non-limiting illustrative example, biological extraction data input and a body degradation function relating the biological extraction data to rates of physiological deterioration as an output.

Further referring to FIG. 2, training data 120 may be filtered, sorted, and/or selected using one or more supervised and/or unsupervised machine-learning processes and/or models as described in further detail below; such models may include without limitation a training data classifier 212. Training data classifier 212 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 120. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 212 may classify elements of training data to match one or more categories including elements of user data and/or degradation rates, such as without limitation a cohort of persons and/or other analyzed items and/or phenomena for which a subset of training data 120 may be selected.

Still referring to FIG. 2, machine-learning module 200 may be configured to perform a lazy-learning process 216 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 120. Heuristic may include selecting some number of highest-ranking associations and/or training data 120 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 220. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 220 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 220 may be generated by creating an artificial neural network, such as a convolutional neural network comprising an input layer of nodes, one or more intermediate layers, and an output layer of nodes. Connections between nodes may be created via the process of "training" the network, in which elements from a training data 120 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 224. At least a supervised machine-learning process 224, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include biological extraction datum 108 as described above as inputs, degradation rates as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 120. Persons skilled in the art, upon reviewing the entirety of this disclosure, will be aware of various possible variations of at least a supervised machine-learning process 224 that may be used to determine relation between inputs and outputs. Supervised machine-learning processes may include classification algorithms as defined above.

Further referring to FIG. 2, machine learning processes may include at least an unsupervised machine-learning processes 228. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 220 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 120 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 120.

Figure 3:
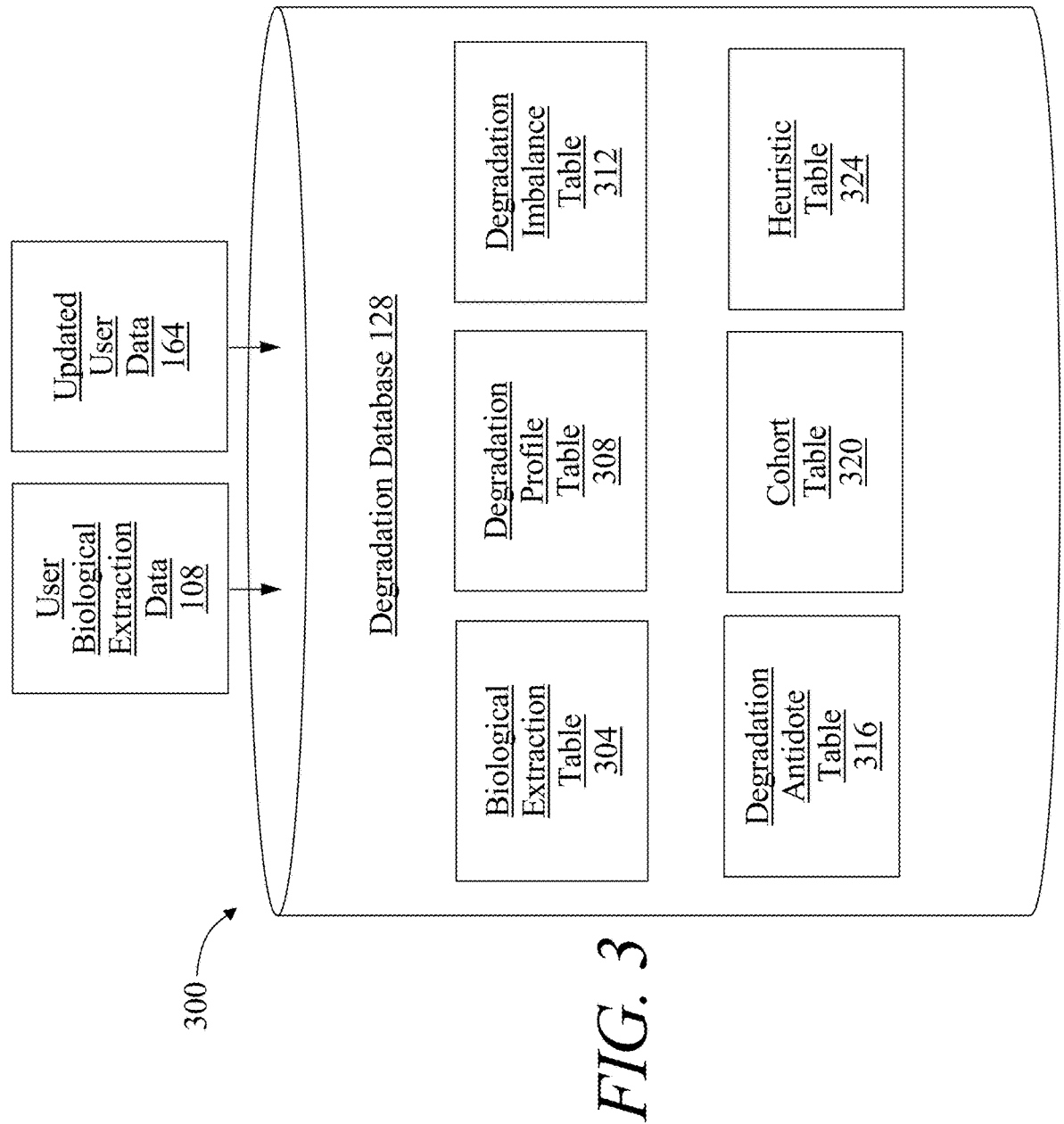
FIG. 3 is a block diagram illustrating an exemplary embodiment of a degradation database.

Referring now to FIG. 3, a non-limiting exemplary embodiment 300 of a degradation database 128 is illustrated. Degradation database 128 may be implemented, without limitation, as a relational database, a key-value retrieval database such as a NOSQL database, or any other format or structure for use as a database that a person skilled in the art would recognize as suitable upon review of the entirety of this disclosure. Degradation database 128 may alternatively or additionally be implemented using a distributed data storage protocol and/or data structure, such as a distributed hash table and the like. Degradation database 128 may include a plurality of data entries and/or records, as described above. Data entries in a degradation database 128 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 3, degradation database 128 may include, without limitation, a biological extraction table 304, degradation profile table 308, degradation imbalance table 312, degradation antidote table 316, cohort table 320, and/or heuristic table 324. Determinations by a machine-learning process, machine-learning model, and/or scoring function may also be stored and/or retrieved from the degradation database 128, for instance in non-limiting examples a classifier describing a subset of users with alike biological extraction data as it relates to biological degradation rates. Determinations by a machine-learning model, for instance for calculating a degradation rate and/or a machine-learning process for determining an antidote strategy, may also be stored and/or retrieved from the degradation database 128. As a non-limiting example, degradation database 128 may organize data according to one or more instruction tables. One or more degradation database 128 tables may be linked to one another by, for instance in a non-limiting example, common column values. For instance, a common column between two tables of degradation database 128 may include an identifier of a submission, such as a form entry, textual submission, degradation rates, and the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, and the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of a degradation database 128 may include, as a non-limiting example, a biological extraction table 304, which may include elements of user biological extraction data, as described above, and any associated data relating to wearable device data, determinations made by an expert, medical professional, physical trainer, or the like, including medical history data, physiological measurements, medical conditions, diagnoses, diseases, or any other factors for use in determining degradation profile 116, rates and/or levels of physiological deterioration, and/or other elements of data computing device 104 and/or system 100 may store, retrieve, and use to determine usefulness and/or relevance of biological extraction data in determining degradation imbalances, degradation antidotes, degradation reduction, prevention, and/or management, as described in this disclosure. One or more tables may include degradation profile table 308, which may include numerical values, functions, vectors, matrices, coordinates, graphical data, parameters, and the like, for instance and without limitation, that link user biological degradation, for instance in determining a current level of degradation, instantaneous rate, and/or projected rates of degradation to one or more physiological categories. One or more tables may include a degradation imbalance table 312, which may correlate degradation rankings, scores, and/or other biological extraction data as it pertains to a determination about an instantaneous degradation rate, current degradation level, or projected degradation rate, and the like, including any outcomes, models, heuristics, scores and/or combinations thereof as they may correspond to rankings, determination, calculations, or combinations of items listed as numerical values, metrics, functions, vectors, matrices, and the like, that corresponds to determining a degradation rate and/or level as it may correspond to a standard, expected, or projected rate and/or level, for instance and without limitation, a user's current degradation profile versus in a 'healthy' individual of similar parameters. One or more tables may include, without limitation, a degradation antidote table 316 which may contain one or more inputs identifying one or more categories of data, for instance a degradation antidote strategy, and/or ranking of degradation antidote strategy steps, expected levels of efficacy, for instance as numerical values, functions, and the like. One or more tables may include, without limitation, a cohort category table 320 which may contain one or more inputs identifying one or more categories of data, for instance demographic data, lifestyle data, physiological data, sleep pattern data, or the like, with regard to which users having matching or similar data may be expected to have similar degradation rates, levels, profiles, degradation imbalances, degradation antidote strategies, and/or instruction sets as a result of a machine-learning process determination, computational simulations, ranking process output elements and/or other data input elements. One or more tables may include, without limitation, a heuristic table 324, which may include one or more inputs describing potential mathematical relationships between at least an element of user data and, for instance and without limitation, degradation rates, levels, profiles, degradation imbalances, degradation antidote strategies, and/or instruction sets as a result of a machine-learning process determination, computational simulation outputs, and rankings thereof, and how they may change as a function of a user's age, as described in further detail below.

Referring back to FIG. 1, computing device 104 may generate at least an expected rate 124 using a degradation machine-learning model 112 trained with training data from a degradation database 128, wherein the at least an expected rate 124 of biological degradation is a mathematical function describing the rate of biological degradation over time. In a non-limiting illustrative example, expected rate 124 may be a function that represents the integrity levels of a certain physiology category of a user that is predicted as a function of determined degradation rates for the life of the user based on the biological extraction data provided. Expected rates 124 for all physiological parameters that body degradations were calculated for may be summarized in the degradation profile 116. Expected rates 124 may be numerical values that correspond to physiological integrity levels and an associated rate of change for each integrity level numerical value. In non-limiting illustrative examples, the function of expected rates may have improved accuracy with increased sampling of points for integrity levels and rates of change; for instance accuracy of one point per year over 60 years (age 20 to age 80) could be increased if sampling for expected rate points was increased to 12 times per year (monthly) for 60 years.

Referring now to FIG. 1, computing device 104 generating the degradation profile 116 may include mapping the biological extraction datum 108 to a plurality of mathematical functions that summarize rates of biological degradation of user physiology. Computing device 104 may generate the degradation profile 116 using a degradation machine-learning model 112, as described above, using training data 120 that trains the model using the biological extraction datum 108 as it relates to degradation rates. The degradation profile 116 may be a summary of the current level of biological degradation and the rate at which the biological degradation is changing, for instance the current capacity of a user's physiological state and may include information about theoretically achievable minimum of degradation. In non-limiting illustrative examples, this may include the user's current level of vision, which may have already degraded since adolescence into adulthood. Degradation rates may refer to mathematical functions of the instantaneous rate of change of degradation level, for instance and without limitation, the current rate at which a user's vision is degrading. In such an example, a user's vision may be degrading based on user lifestyle parameters such as electronic device usage, time spent reading, and other biological extraction data such as nutrition deficiencies in lutein, zeaxanthin, vitamin C, vitamin E, and essential fatty acids, sleep quality, among other data. A degradation machine-learning model 112 may be trained with this data and/or other data, for instance and without limitation, stored and/or retrieved from a degradation database 128 that corresponds to rates of degradation related to parameters located in the biological extraction data. For instance and without limitation, research published that links chronic nutritional deficiencies and/or time spent on electronic devices related to a concomitant decrease in visual acuity and presence of astigmatism in vision. In such an example, a degradation machine-learning model 112 may be trained with this data and determine from the biological extraction data a range of expected rates where the user's vision degradation may be described by a mathematical function that describes the spectrum of relationships determined from the data. Computing device 104 may use such a machine-learning model to map the biological extraction data to a plurality of mathematical functions that summarize rates of degradation of user physiology, wherein at least an element of biological extraction data may have associated with it a current level of degradation, an instantaneous rate, and a proposed, extrapolated, predicted, otherwise determined degradation rate extending forward in time into the future.

Referring back to FIG. 1, computing device 104 generating a degradation profile 116 may calculate a biological degradation function of a user that is a mathematical function that describes the change in rate of degradation over time corresponding to the degradation data. A degradation machine-learning model 116 may map user biological extraction data to expected rates of deterioration in physiological categories, as described above. Mapping may include plotting the calculated "integrity" of the physiological category, wherein integrity is a relative measurement that corresponds to the upper limit and lower limit of a physiological category, for instance, visual acuity. In non-limiting illustrative examples, the degradation machine-learning model 116 may plot the mathematical relationship between the user biological extraction data to the percent integrity of a user's vision; wherein the 100% integrity upper limit may correspond to the maximal visual acuity a person may have without surgical intervention, corrective lens, and the like; alternatively or additionally, the 100% integrity may be the upper limit once surgical intervention, corrective lens, and the like were adopted. In such an example, the degradation machine-learning model 116 may map the user's current biological extraction data, such as lifestyle data as it pertains to use of vision, to the percent integrity of visual acuity over time as is expected according to the current level, instantaneous rate of change, and expected rate of change if user biological extraction data was unaltered.

Figure 4:
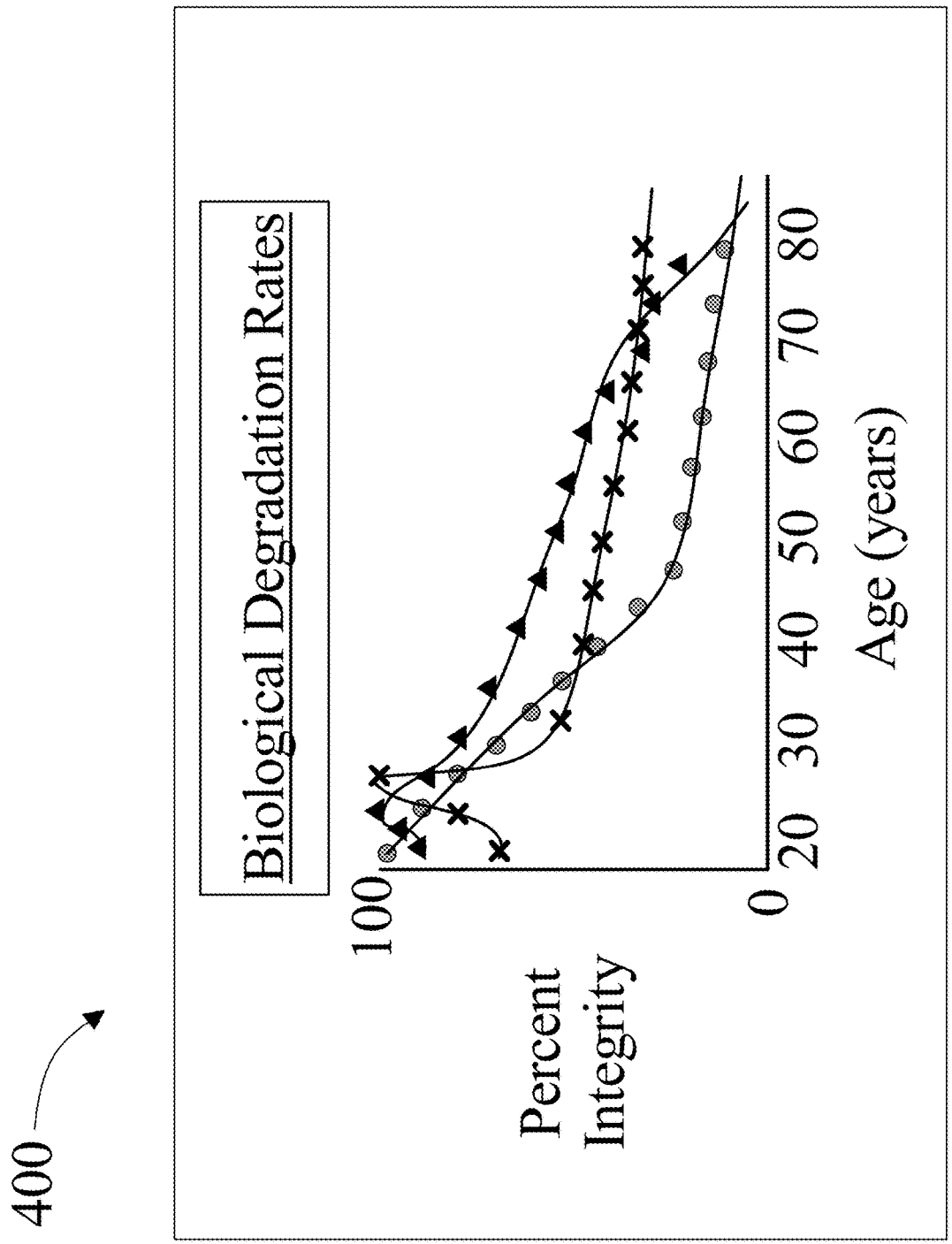
FIG. 4 a diagrammatic representation illustrating an exemplary embodiment of mathematical functions describing biological degradation rates.

Referring now to FIG. 4, a non-limiting exemplary embodiment 400 of mathematical functions that describe the change in rate of degradation over time corresponding to the degradation data is illustrated. Three categories of biological degradation (denoted by circle, triangle, and X) are plotted as their percent integrity as a function of time, or age of user in years. Each point may be a sample extrapolated calculation for the percent integrity where at that time in years training data 120 for a degradation machine-learning model 112 may have be located that could accurately predict the percent integrity of the user's physiology given a determined rate of degradation. In non-limiting illustrative examples, training data 120 may have been located that describes the integrity of a user's mental plasticity as the user ages; for instance where training data was located for how mental plasticity may degrade over the life of a user every 5 years from the time a person is 20 years of age until they are 80 years of age. In further non-limiting examples, given the user's current level of education, lifestyle, genetic and epigenetic analysis, among other data, a degradation machine-learning model 112 may determine that the percent integrity of the user's mental plasticity may be graphed as the curve denoted by X's in FIG. 4, wherein the percent integrity of mental plasticity improves moderately throughout the user's 20's wherein the user is attending post-secondary education and obtaining a professional degree, constantly challenging and exercising their cognitive abilities reaching an upper limit near the age of 30. In such an example, it may be determined by the machine-learning model that they user is expected to encounter a rapid decrease in integrity of mental plasticity through their 30's and 40's into midlife due to the sudden loss of scholastic environment, rapid lifestyle changes such as raising children, changes in gene expression patterns and DNA methylation, lack of cognitive exercise, decrease in sleep quality, among other biological and lifestyle phenomena. Correspondingly, in this example, the current level of degradation as a numerical value can be determined at any point in time, including the instantaneous rate of change in integrity at any point in time and a graphical trace of the expected integrity of the physiological parameter. In non-limiting examples, a degradation profile 116 may be a summary of numerous mathematical functions of percent integrity of physiology and the associated biological degradation over time through a user's life; wherein the degradation profile 116 may contain numerical data of the current level, instantaneous change at every year of age, and the full predicted function that is the integrity change over time which accurately conveys determinations by the degradation machine-learning models 112.

Figure 5:
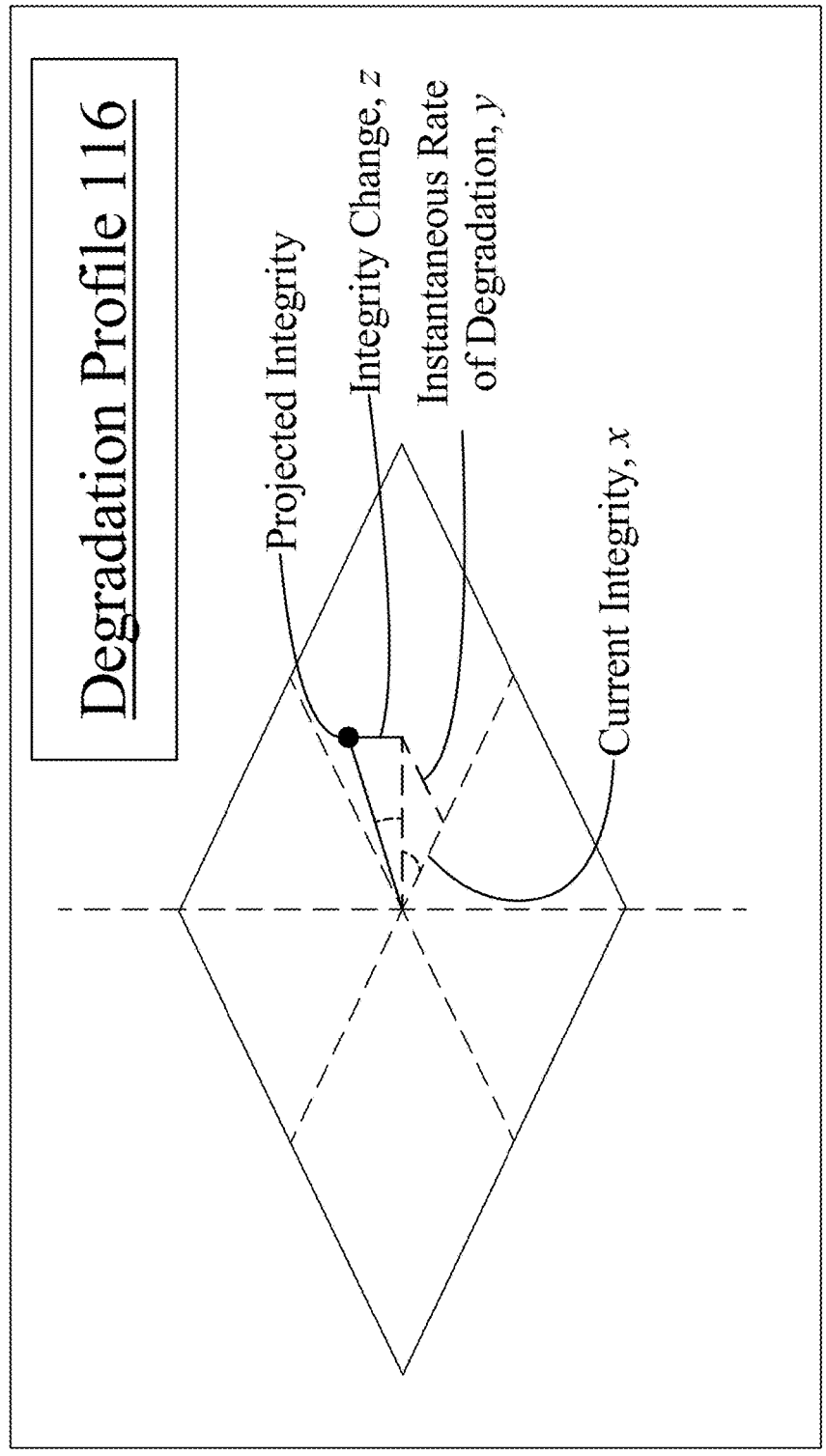
FIG. 5 is a diagrammatic representation illustrating an exemplary embodiment of a graphical representation of a degradation profile.

Referring now to FIG. 5, a non-limiting exemplary embodiment 500 of a single physiological element of a degradation profile 116 is illustrated. In non-limiting illustrative embodiments, the current percent integrity of a user's physiological function, instantaneous rate of change, and/or projected integrity at any point in time may be described as a series of polar coordinates in a Gaussian plane. As FIG. 5 illustrates, each physiological category may be represented as a point and/or series of points in a single-dimensional, two-dimensional, and/or three-dimensional Gaussian plane, wherein each dimension may relate to a parameter of the physiological integrity for that category. In the non-limiting illustrated example, a degradation profile 116 may be represented by any number of polar coordinates, for instance and without limitation in 3-dimensions, describing the current integrity, change in integrity, and projected integrity at any time, among other parameters calculated and/or considered by a machine-learning process and/or machine-learning model. Alternatively or additionally, degradation profile 116 categories may be represented by vectors, functions, matrices, or any other numerical value or form that can be used to mathematically describe biological phenomena summarized in a degradation profile, as described above. In the example presented in FIG. 5, the angles between parameters may represent mathematical relationships between other physiological categories in the degradation profile, for instance the plasticity of a category and/or its propensity to be changed by biological extraction parameter and/or lifestyle effects. The degradation profile 116 may be composed of a plurality of individual physiological categories and their respective degradation rates.

Referring back to FIG. 1, computing device 104 may identify, using a degradation imbalance machine-learning process 132 and the degradation profile 116, a degradation imbalance 136, wherein a degradation imbalance 136 is a rate of biological degradation that exceeds a preconfigured threshold value 140. A "threshold value," as used herein, refers to a theoretical integrity level, theoretical rate of change, and theoretical integrity function for a user according to a degradation machine-learning model 112 trained with training data 120 that determines what the 'percent integrity' of a user's physiology and rate of biological degradation that may be theoretically predicted of a 'healthy' individual that most closely matches the user's sex, age, height, fitness level, medical history, among other biological extraction parameters; otherwise a 'scientifically achievable' threshold value. For instance, in non-limiting illustrative examples, the preconfigured 'threshold value' for bone density may be the predicted rate of bone density deterioration, degradation, and/or change of rate, that would be anticipated of bone density level over time and the associated rate of degradation. Such a preconfigured threshold value may be determined using a standard rate machine-learning model 144 trained with training data 120 that corresponds to a subset of users identified by, for instance and without limitation, a classifier. A standard rate machine-learning model 144 may be trained using training data 120 by a machine-learning module, including using a machine-learning process, as described above. The threshold value may be a number, quantitative, value, or function of values, stored in computing memory to be used to determine if a change in a biological extraction parameter represents a decrease or increase in degradation.

Deviation above or below such a threshold value may indicate that there is an increased or decreased rate of degradation. For instance in non-limiting illustrative examples, degradation machine-learning model 112 may determine that, given the user's biological extraction data and any accompanying data that may be retrieved from a degradation database 128 regarding degradation over time, that if the user maintains a similar level of physical activity, they can expect a particular level of muscular endurance integrity throughout their life. In such an example, the level of muscular endurance integrity may be graphed as a function of percent integrity over time, wherein the year-to-year change is due to a degradation rate determined by the machine-learning model, and the corresponding associated values and physiological categories in the degradation profile 116. Additionally, in non-limiting illustrative examples, standard rate machine-learning model 144, may determine a threshold value by training with training data 120 corresponding to alike users with physiology like a first user using a classifier, as described above, to determine the predicted degradation rate and integrity levels over time for an idealistic, 'healthy' individual; otherwise, a machine-learning model may determine the upper limit with associated confidence levels for the degradation rate and the integrity level for a 'healthy' version of the user. In such an example, a 'healthy' user may represent an idealistic physiology where the percent integrity represents improvement of body degradation to an allowable genetic upper limit according to potential degradation antidote strategies, scientific results, medical histories, data from other users, and the like. The degradation values associated with the threshold value from the standard rate machine-learning model 144 may be compared to the degradation values associated with the degradation profile 116 to determine if any difference between values exists, wherein a difference may represent a degradation imbalance 136.

A "degradation imbalance" as used in this disclosure, refers to a numerical difference between the current and/or projected physiological integrity and biological degradation obtained from a user's preconfigured 'threshold value' from that of the physiological integrity and biological degradation in the biological profile 116 of a user. In non-limiting illustrative examples, theoretical threshold values may be per-user calibrated using the standard rate machine-learning model 144 and training data 120 that is selected using a classifier that corresponds to alike user physiology and/or retrieved from online repository, published data, and the like. A degradation imbalance may be calculated by a degradation imbalance machine-learning process 132, for instance and without limitation, by taking determinations by the machine-learning models, as described above, and performing a mathematical operation, such as subtraction, of the threshold values from the expected rates. In non-limiting illustrative examples, subtraction of the expected rates from the threshold values may provide a variety of numerical values, wherein positive values may represent imbalances where the expected rate falls short of the threshold value, and negative numbers represent areas where a user's body degradation rate is below the expected rate for the 'healthy' threshold value. In such an example, the degradation imbalance machine-learning process 132 may be prompted to query for degradation antidote strategies based upon the numerical value calculated and whether it indicated an imbalance.

Continuing in reference to FIG. 1, computing device 104 identifying the degradation imbalance 136 may calculate a numerical difference between the threshold value 140 of biological degradation generated by the standard rate machine-learning model 144 with the biological degradation rates in the degradation profile 116. A degradation imbalance machine-learning process 132 may determine differences between degradation rates, integrity level, degradation profiles between users, and/or any other determinations, as described above, generated by the degradation machine-learning model 112 and the standard rate machine-learning model 144. Calculating a numerical difference may be any mathematical operation to determine a difference, for instance and without limitation, subtraction of a series of values between two functions. Calculating a numerical difference may involve analysis of differences present in two data sets, for instance and without limitation, solving a system of equations wherein regions between functions may represent an imbalance; calculating derivatives of functions, wherein inflection points, local minima, local maxima, and the like, represent numerical values that may be compared between functions to determine degradation imbalances.

Figure 6:
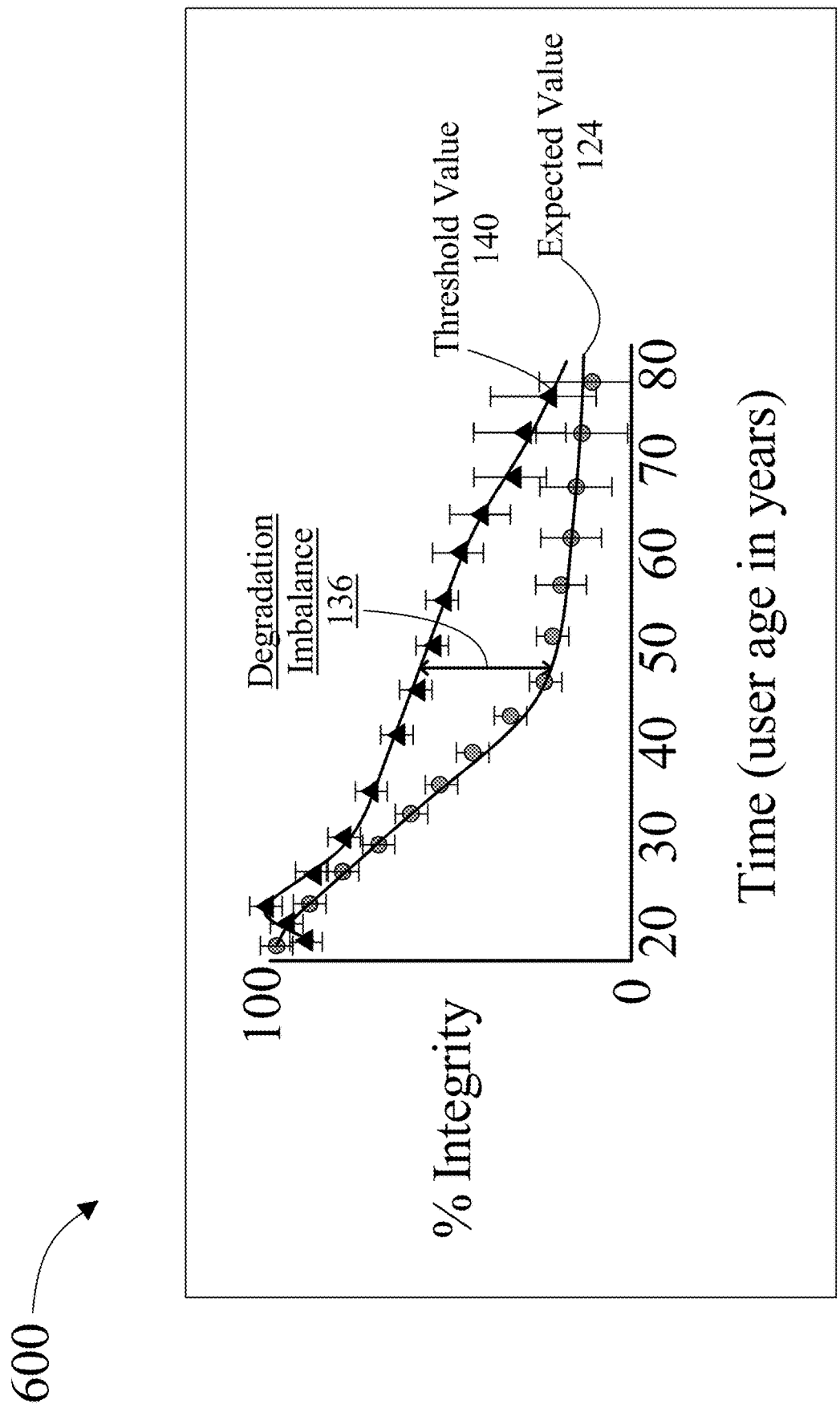
FIG. 6 is a diagrammatic representation illustrating an exemplary embodiment of a degradation imbalance.

Referring now to FIG. 6, a non-limiting exemplary embodiment 600 of a determined degradation imbalance 136 is illustrated. FIG. 6 illustrates two curves plotted as means±standard deviations, a current body degradation rate from a degradation profile 116 (denoted by circles) and an expected degradation rate (denoted by triangles). In such an example, the 'threshold value degradation rate' may refer to the theoretical 'healthy' individual values according to the user's biological extraction as generated by the standard rate machine-learning model 144. In non-limiting illustrative examples, the threshold value curve may represent the values of degradation if a user were to implement a suggested degradation antidote strategy, as described in further detail below. The 'expected rate degradation profile rate' represents the expected rate of degradation, as generated by the degradation machine-learning model 112 based on current user biological extraction data. A degradation imbalance machine-learning process 132 may calculate at different time samplings along the curves, wherein at each sampling the degradation imbalance machine-learning model 128 may qualitatively and/or quantitatively assess any difference between a user's body degradation and the expected degradation rate, wherein any difference may reflect an imbalance wherein the user's rate of body degradation exceeds what would be expected. The statistical parameters illustrated in FIG. 6 by error bars may reflect the certainty in the parameters determined by the machine-learning models; wherein as the time sampling is further away from a user's current age, the certainty in the values decreases as evidenced by larger error bars.

Referring back to FIG. 1, computing device 104 identifying the degradation imbalance may include determining if the numerical difference between the threshold value 140 of biological degradation and the degradation profile 116 correlates to a degradation imbalance 136. Degradation imbalance machine-learning process 132 calculating a difference between a threshold value 140 and a value in the degradation profile 116 may determine if any numerical difference between values correlates to a degradation imbalance 136. A numerical difference which represents a level of degradation, degradation rate, and/or expected rate in the degradation profile 116 that falls below the threshold value 140 may illustrate a degradation imbalance. In non-limiting illustrative embodiments, degradation imbalance machine-learning process 132 determining if a calculated difference correlates to a degradation imbalance 136 may include determining statistical significance of a numerical difference, for instance and without limitation, using confidence intervals, p-values, or any other calculated statistical evaluation that determines statistical significance. In further non-limiting illustrative embodiments, a statistically significant difference between a threshold function and a biological degradation function of a user may illustrate a degradation imbalance 136, wherein the user's physiology is deteriorating at a pace faster than would be expected if the individual were healthy. Machine-learning models may be trained such that the functions they are trained to form have confidence intervals for threshold values, expected rates, and the like, wherein comparing a difference between any two will allow adequate statistical evaluation.

Continuing in reference to FIG. 1, computing device 104 may determine, as a function of the degradation imbalance machine-learning process 132 and the degradation imbalance 136, a degradation antidote strategy 148 to decrease the rate of biological degradation of a user. A "degradation antidote strategy," as used in this disclosure, is a strategy that a user may employ to decrease at least a rate of body degradation for at least a single physiological category. A degradation antidote strategy 148 may be stored and/or retrieved from a degradation database 128 by a degradation imbalance machine-learning process 132. Degradation antidote strategy 148 may be a numerical value, function, text submission, graphical representation of data, or any other suitable format of information that corresponds to data that refers to a way to decrease a rate of body degradation.

Continuing in reference to FIG. 1, computing device 104 determining a degradation antidote strategy 148 may perform a simulation 152, wherein the simulation randomly perturbs a parameter, and wherein a parameter is an element of numerical data relating to the at least a user biological extraction datum 108.

Continuing in reference to FIG. 1, a simulation 152 may refer to performing any computational algorithm, method, or the like, that may generate an output, of a plurality of outputs, given a range of input values that the simulation algorithm may select—in a random and/or guided manner— to provide a plurality of observations, outputs, or the like, wherein the nature of the outputs may not entirely known and/or predicted. Simulation 152 may be a stochastic simulation process such as Markov Model Monte Carlo (MMMC) simulations, McKean-Vlasov processes, Monte Carlo localization, stochastic tunneling, among other probabilistic stochastic heuristics that randomly select numerical parameters from within a defined set of parameters and calculate an outcome for all selected parameters. Simulation 152 may be a probabilistic technique for approximating global optimum of a given function, matrix, vector space, or the like, such as simulated annealing algorithm, interacting Metropolis-Hasting algorithms, quantum annealing, Tabu search, Dual-phase evolution, reactive search optimization, and the like.

Simulation 152 may refer to a "Monte Carlo simulation" may refer to a "Monte Carlo method," "Monte Carlo experiment," and/or performing a "Monte Carlo algorithm." A Monte Carlo simulation is a mathematical technique that may generate variables, numerical values, and the like, for modeling risk, outcomes, uncertainty, etc., of a certain system using a stochastic simulation process. Monte Carlo simulations may encompass a range of algorithms and mathematical analysis techniques such as Markov Model Monte Carlo (MMMC) simulations, McKean-Vlasov processes, Monte Carlo localization, among other probabilistic stochastic heuristics that randomly select numerical parameters from within a defined set of parameters and calculate an outcome for all selected parameters. In non-limiting illustrative examples, a Monte Carlo simulation may generate a series of numerical values represented by traces, curves, functions, and the like, wherein each function may represent a sufficiently good solution and/or outcome to an optimization problem, wherein the solution may be represented by a polar coordinate, vector, function, or the like, that represents a body degradation of a physiological category of a user over time depending on how the user's biological extraction data may change. Each generated body degradation curve may have associated with it changes in biological extraction data. For instance in non-limiting illustrative examples, a simulation may determine a large degree of curves tracing how a user's skin integrity degrades over time for different values of sleep quality, use of collagen supplements, applying topical moisturizer containing a variety of active ingredient concentrations, and the like; wherein each curve may be a series of numerical values of percent integrity plotted as a function of time for a wide variety of average hours of sleep each night, sampled in 1-hr increments, and mg/kg amounts of collagen supplementation, sampled in 1 mg/kg increments. And thus, each parameter may have an estimated degradation rate associated therewith. Moreover, each physiological category may have a simulation performed for each biological extraction datum that is associated with it.

In a non-limiting exemplary embodiment, Monte Carlo simulation is a class of computation algorithms used by a machine-learning process that may rely on repeated random sampling of parameters to obtain numerical results, for instance generating body degradation curves as a function of randomly sampling biological extraction data values. Monte Carlo simulations may be performed with dynamic systems that may be coupled with an analysis method. For instance and without limitation, in the case of random sampling of biological extraction parameters relative to body degradation rates, wherein the biological extraction parameter sampling may be refined within the simulation by a machine-learning process which may recognize more optimal results and the numerical values corresponding to the more optimal results. In non-limiting illustrative examples, a machine-learning process, such as a supervised machine-learning process, may accept generated candidate biological extraction parameters and subsequent body degradation traces from a Monte Carlo simulation, as described above, and determine how these parameters relate to the current biological extraction data. In non-limiting illustrative examples, a machine-learning process may recognize that increases in numerical value of a particular biological extraction parameter is generating traces that are decreasing degradation rate. In such an example, the machine-learning process may log those biological extraction parameters for refining the simulation, confining the simulation to numerical values of the parameter that exceed the user's current biological extraction parameter.

Simulation 152 may generate many biological extraction parameters, where a machine-learning process may narrow the number of biological extraction parameters based on their effect on body degradation. Such a machine-learning process may iteratively determine how these parameters compare to the user's input biological extraction data, for instance and without limitation, the simulation 152 generates degradation curves showing that increased levels of sleep improve a user's cognitive ability, wherein the machine-learning process may also recognize that the amount of time cannot exceed 24 hours in a 24 hour period. In this example, the machine-learning process may iteratively refine the simulation to sample sleep parameters under 24 hours per day but greater than the current amount of sleep. Alternatively or additionally, the machine-learning process may direct the simulation 152 to select the sleep parameter that resulted in the greatest decrease in body degradation to move forward and combine with a second category of parameter to run a subsequent simulation.

Continuing in reference to FIG. 1, computing device 104 performing the simulation 152 may include sampling user biological parameters and performing a simulated degradation function, measuring a change in biological degradation as a function of the simulated degradation function, and determining a parameter aggregate that results in the most decreased degradation rate. In non-limiting illustrative examples, a simulation 152 may sample biological parameters using a mathematical operator, scalar, or any other mathematical manipulation to the given parameter numerical value, for instance sampling a range of 0.05-20 times of a biological parameter; in such an example a simulation 152 may select parameters for a nutritional supplementation for body degradation and randomly select ¹⁄₂₀ to 20 times a nutritional supplement that a user is currently. Continuing in the above example, after a sufficient number of trials, the simulation 152 may be guided by a machine-learning process in finding that values 10 times and more of the current value is more optimal; however, the machine-learning process may retrieve information from a database that dictates the maximal acceptable dose is 50 times the current dose. In such an example, the machine-learning process may guide the simulation 152 to sample between 20-40 times the current dose of a nutritional supplement, with simulations run in increments of 0.25 times, for a total of over 80 simulations. For each simulation, the simulation 152 may be performed for a range of time, for instance every week of the year for a total of +2 years from present time, for a total of over 100 time point samplings for each simulation. The machine-learning process may then determine which trace, curve, function, and the like, and thus which biological extraction parameter, resulted in the best outcome for each batch of simulations, wherein the 'best outcome' corresponds to the maximal decrease in body degradation rate.

Continuing in reference to FIG. 1, computing device 104 may determine which parameters result in the maximal decrease in degradation rate and match the parameter that resulted in the maximal decrease in degradation rate with a concomitant change in user biological extraction data. Degradation imbalance machine-learning model 128 may determine which parameters from the simulation 152 result in the largest decrease in degradation rate. This may be accomplished, for instance and without limitation, by graphing the outputs of the simulation 152 of change in degradation rate over time, change in integrity over time, or any other way to quantitatively evaluate the simulation 152 outputs relative to one another.

Figure 7:
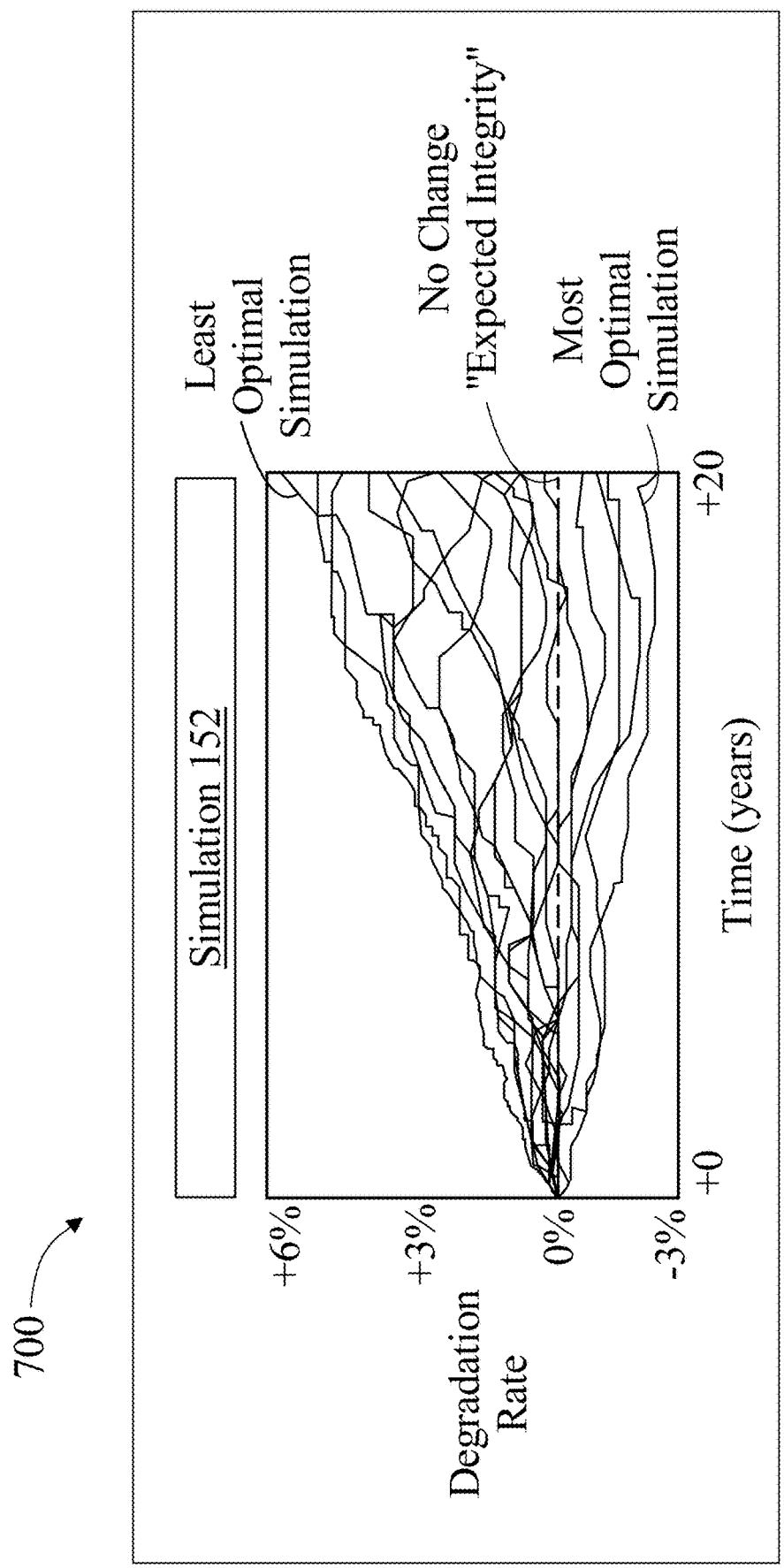
FIG. 7 is a diagrammatic representation illustrative an exemplary embodiment of a simulation.

Referring now to FIG. 7, a non-limiting illustrative embodiment 700 of the outputs of a simulation 152 for sampling a single biological extraction parameter for changes in degradation rate as a function of time. Each trace in the graph represents a single simulated experiment wherein a selected biological extraction datum was randomly altered and the degradation rate of a physiological category was calculated, for instance every week over a 20 year period for a user (1,024 data points per trace). Degradation imbalance machine-learning process 132 may determine which trace, and thus which biological extraction parameter, results in the largest decrease in degradation, denoted in FIG. 7 as 'most optimal simulation'.

Referring back to FIG. 1, computing device 104 determining which biological extraction parameters results in a maximal decrease in degradation rate may do so by using the degradation imbalance machine-learning process 132 to determine the most optimal simulation by, for instance and without limitation, numerically ranking the outputs using a scoring function, performing mathematical operations to calculate numerical differences, and/or graphically representing the simulations as shown in FIG. 7. In non-limiting illustrative examples, a degradation imbalance machine-learning process 132 may categorize, sort, or otherwise rank simulation output parameters as aggregates of parameters ranked by effect on degradation rate; ranking may be for instance numerical ranking where the machine-learning process generates a table of parameters ranked in descending order from most effective to least effective and stores the values in a degradation database 128. In such an example, a machine-learning process may be able to query the ranked and sorted aggregate parameters to select parameters that correspond to the maximal decrease in degradation rate.

Continuing in reference to FIG. 1, computing device 104 matching simulation parameters to biological extraction parameters may include using the degradation imbalance machine-learning process 132 to calculate a numerical difference between the simulated parameters and the current user biological extraction parameters. As described above, the biological extraction parameters that result in the maximal decrease in body degradation rate may be compared to current user biological extraction using a mathematical operation, for instance and without limitation, subtraction. In non-limiting illustrative examples, degradation imbalance machine-learning process 132 may accept an input of the selected aggregate parameters from a plurality of Monte Carlo simulations and compare each parameter to the cognate value present in the current biological extraction data. In non-limiting illustrative examples, simulated parameters that result in maximal decrease in body degradation may be that the user should get an average of 9.2 hours of sleep per night, take 500 mg of vitamin C daily, and devote 3 hours to memory training per week, and the degradation imbalance machine-learning process 132 may compare these numerical values to the current user biological extraction data and find that the user has a deficit of an average of 2.3 hours of sleep per night, a deficit of 300 mg of vitamin C per day, and a deficit of 1.5 hours of memory training per week. In exemplary illustrative embodiments, the degradation imbalance machine-learning process 132 may match on the order of 100-1000 s or more of biological extraction data parameters, as an aggregate of parameters extracted from the Monte Carlo simulations, to the biological extraction data provided by a user; at least a single biological extraction datum would be necessary for the simulation, but the method may be adaptable to large-scale simulation of a high degree of parameters.

Continuing in reference to FIG. 1, computing device 104 may determine a degradation antidote strategy 148 to decrease the rate of biological degradation of a user using the simulated aggregate parameters and how they compare to current user biological extraction data. Degradation imbalance machine-learning process 132 may determine a degradation antidote strategy 148 to decrease body degradation rates by taking calculated deficiencies, mismatches, and/or inadequacies found in the user biological extraction data, as described above, and query for strategies, methods, and/or interventions that may address the gap in biological extraction parameters. In non-limiting illustrative examples, an average of 2.3 hours of sleep per night may be addressed by a strategy for improving sleep quality, a deficit of 300 mg of vitamin C per day may be addressed by nutritional supplementation, and a deficit of 1.5 hours of memory training per week may be addressed by purchasing and setting aside time each week for drilling with the memory flash cards. Degradation imbalance machine-learning process 132 may locate such strategies by, for instance and without limitation, querying an online repository of data, such as a research database, expert submissions, blog posts, commercial adverts, product lines, social media, among many other web-based and non-web-based informational sources. Computing device 104 may have access to these sources, among others, by being a part of a network, as described in further detail below.

Continuing in reference to FIG. 1, computing device 104 determining the degradation antidote strategy 148 may include retrieving from a database 124, a strategy for reducing the rate of degradation. Degradation machine-learning process 132 may store and/or retrieve degradation antidote strategies from a degradation database 128. Degradation machine-learning process 132 may query a degradation database 128, as described above, for strategies to address difference between biological extraction parameters and optimal aggregate parameters. Degradation antidote strategy 148 may be retrieved from peer-reviewed publication, blog post, expert submission, research repository, web-based query, or any other suitable location where a strategy for altering body degradation may be located by a computing device; persons skilled in the art, upon reviewing the entirety of this disclosure, will be aware of various locations in which degradation antidote strategies may be retrieved. For instance and without limitation, a degradation antidote strategy 148 may be retrieved from a degradation database 128 using a query by a degradation imbalance machine-learning process 132, wherein the query is based on using a classifier that describes a subset of users with similar body degradations, biological extraction data, and/or other alike parameters. In further non-limiting illustrative examples, a machine-learning process may compare Monte Carlo simulation outputs from two or more users that result in similar degradation trajectories, including retrieving degradation antidote strategies 148 for a second user according to the what worked for a first user with alike simulations.

Continuing in reference to FIG. 1, computing device 104 determining the degradation antidote strategy 148 may include calculating an effect of the at least a strategy on a degradation imbalance 136, wherein calculating an effect includes determining a numerical value that described the impact of the strategy on the imbalance. The effect of a degradation antidote strategy 148 may be determined by determining an impact that a strategy may have on parameters in the biological profile 116, such as degradation rates, physiological integrity, and the like. Determining an impact may include calculating a numerical value that correspond to the impact. For instance and without limitation, a calculated effect of a strategy on a degradation imbalance 136 may be a numerical value that may be a function describing a dampening of a decrease in integrity over time. In non-limiting illustrative examples a user's joint integrity may be represented by expected rates of degradation relating to loss of integrity of the joints per year as: −1%, −1%, −1%, −2%, −2%, −3%, −3%, −4%, −4%, −4% for the next decade, but once a degradation antidote strategy is implemented these values may be expected to change to: −1%, −1%, −1%, −1%, −1%, −2%, −2%, −2%, −2%, −3%. In such an example, determining the degradation antidote strategy included calculating the effect the on joint integrity each year as: 0%, 0%, 0%, 1%, 1%, 0%, 1%, 1%, 2%, 1%, where each value is an absolute value of integrity amount each year that is expected to be improved by decreasing the degradation rate.

Continuing in reference to FIG. 1, computing device 104 determining the degradation antidote strategy 148 may select a degradation antidote strategy 148 based on the calculated impact. In non-limiting illustrative examples, degradation imbalance machine-learning process 132 may calculate impact scores for each strategy for a plurality of strategies, may store and/or retrieve values related to impact from a degradation database, and then may select a strategy based on the calculated impact. In such an example, degradation imbalance machine-learning process 132 may weight, score, or otherwise rank, strategies for selection based on the calculated impacts.

Continuing in reference to FIG. 1, computing device 104 determining the degradation antidote strategy 148 may include ranking, using a ranking function, steps of the degradation antidote strategy 148, wherein ranking includes weighting the steps based on at least a criterion. Degradation machine-learning process 132 may use an input of a selected degradation antidote strategy 148 and use a ranking function 156 to generate a series of steps of a degradation antidote strategy 148. Steps of a degradation antidote strategy 128 may refer to actions that can be provided to a user as instructions to implement the strategy. For instance, in non-limiting illustrative examples, a degradation antidote strategy 128 may suggest increasing average daily sleep amount by 2.3 hours. In such an example, steps to increasing sleep amount by 2.3 hours may be to take 10 mg of melatonin 1 hour prior attempting to sleep, take a warm bath 45 min before prior attempting to sleep, and to implement this method 2.5 hours before the user would normally try to sleep. In this example, the order in which the steps may be provided to the user are determined by a ranking function 156.

Continuing in reference to FIG. 1, computing device 104 may rank the steps of a degradation antidote strategy 148 by generating a logical order of steps of the degradation antidote strategy for a user to follow. A logical order may relate to the ability of a user to follow the steps in implementing a degradation antidote strategy 148. Logical ordering may be based on difficulty, time, effort, effect, and the like. Generating a logical order of steps may refer to a chronological order of steps, wherein a first step may require being performed prior to a second step. Alternatively or additionally, a logical ordering of steps may be a ranking of steps based on difficulty, wherein difficulty refers to capital investment, for instance and without limitation, purchasing a gym membership, difficulty may refer to level of effort required on behalf of user, deviation from current lifestyle, and the like.

Continuing in reference to FIG. 1, computing device may provide the ranked steps of a degradation antidote strategy 148 for a user as a degradation antidote instruction set 160. Degradation imbalance machine-learning process 132 may perform a ranking function using a ranking algorithm, weighting function, or the like, as described above, to rank the steps of a degradation antidote strategy 148 and retrieve, for instance and without limitation from an online research database, expert submission, degradation database 128, or the like, instructions regarding how to implement the ranked steps of the strategy. In non-limiting illustrative examples, instructions may be steps proscribed to other users with alike degradation antidote strategies 148. Alternatively or additionally, instructions may be determined based on a query of an online source performed by the degradation imbalance machine-learning process 132 and sorted based on difficulty, feasibility, rate of adoption by other users, or the like, and provided to a user for addressing a degradation rate.

Figure 8:
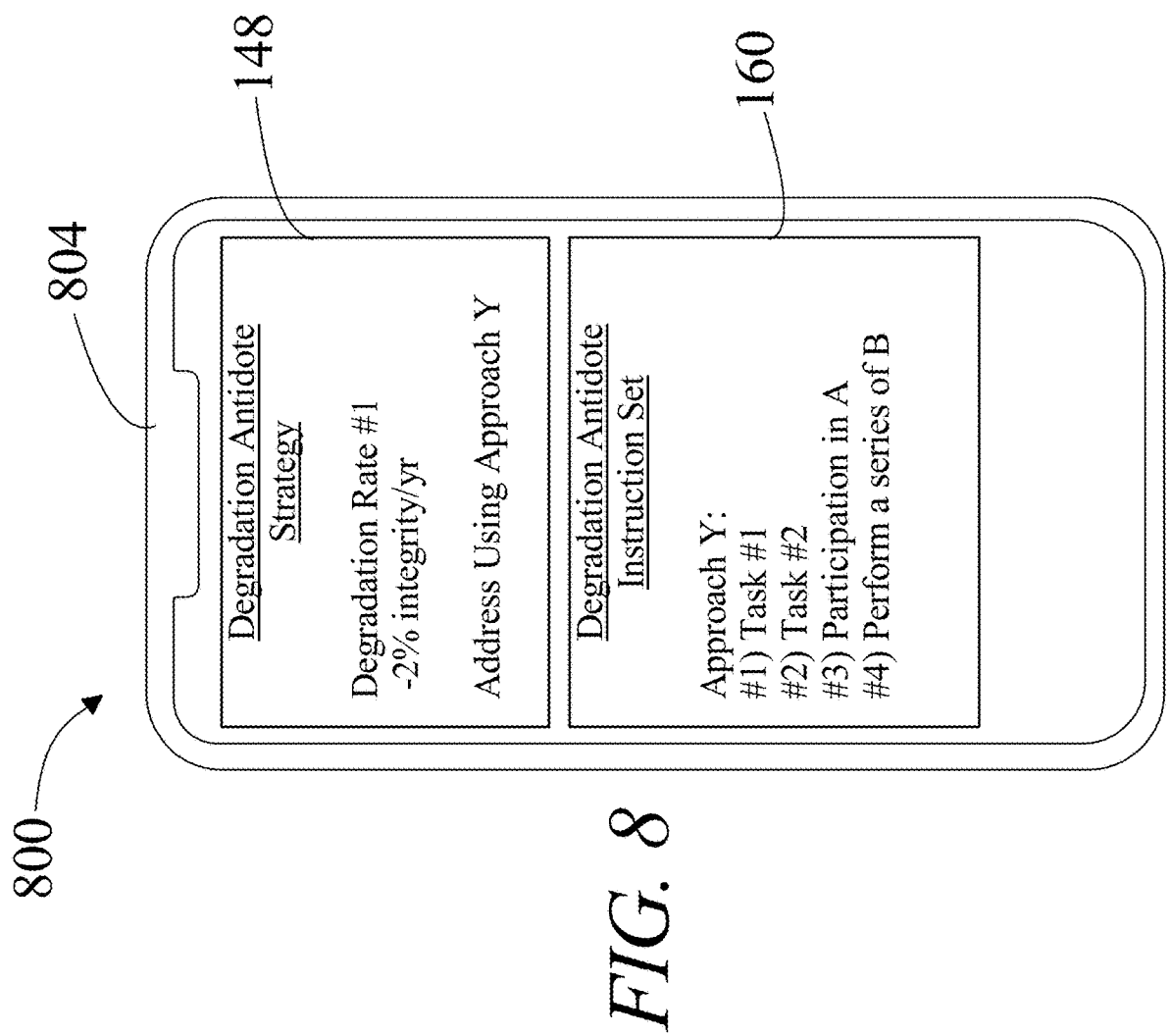
FIG. 8 is a diagrammatic representation of an exemplary embodiment of a graphical display of a degradation antidote instruction set to a user device.

Referring now to FIG. 8, a non-limiting exemplary embodiment 800 of a computing device 104 displaying to a user, using the degradation antidote strategy 148 and the degradation machine-learning process 132, a degradation antidote instruction set 160, wherein the instruction set is a logical order of steps for a user to change in user biological extraction data decrease according to the simulation is illustrated. Computing device 104 may display the degradation antidote strategy 148, degradation antidote instruction set 160, among other parameters, graphics, and determinations performed by system 100 to a user via a user device 804, wherein a user device 804 may be a smartphone, computer, tablet, laptop, TV, or any other electronic device suitable for displaying text, graphics, or the like, via a graphical user interface (GUI), or any other suitable interface, as described in further detail below. Persons skilled in the art, upon reviewing the entirety of this disclosure, will be aware of various ways in degradation antidote instruction sets 160, among other outputs form system 100, may be displayed to a user device 804 and what devices may be usable as a user device 804.

Referring to FIG. 1, computing device may receive updated user data 164, wherein updated user data 164 is user data provided more recent in time than a first degradation antidote instruction set that was provided to a user. Computing device 104 may train a degradation machine-learning model 112 with training data that corresponds to the updated user data 164 as it compares to user biological degradation rates, as described above. Computing device 104 may calculate, using the degradation machine-learning model 112 trained with updated user data 164, a numerical difference between the user degradation profile 116 and the updated biological degradation rates from the updated user data 164. Computing device 104 may recalculate at least a biological degradation rate and a user biological profile, as described above, with the more recent updated user data 164. In a non-limiting illustrative examples, a calculation may be performed by a degradation imbalance machine-learning process 132, which may show that the updated user data 164 resulted in a slowing of body degradation in at least a physiological category, for instance by a decreased degradation rates.

Continuing in reference to FIG. 1, computing device 104 may determine if a parameter in the updated biological extraction data 164 resulted in a numerical difference between the updated biological degradation rates and the user biological profile from the degradation antidote instruction set 160. Computing device 104 may perform such a determination using a degradation imbalance machine-learning process 132, wherein the machine-learning process may determine if calculated difference in, for instance and without limitation, a degradation rate is due to a difference in the user data that corresponds to each degradation rate. Computing device 104 may determine if the indicated change in user data reflects a difference in a biological extraction datum that resulted from adhering to a degradation antidote instruction.

In non-limiting exemplary embodiments, a user device 804 may prompt a user to select degradation antidote instructions, wherein selecting may refer to indicating if an instruction was performed. Selection may be achieved via a user interface, as described above. Selection may inform a degradation imbalance machine-learning process 132 which instructions have been performed for determining if a calculated difference in degradation rate, biological extraction data, and the like resulted from the instruction indicated.

Figure 9:
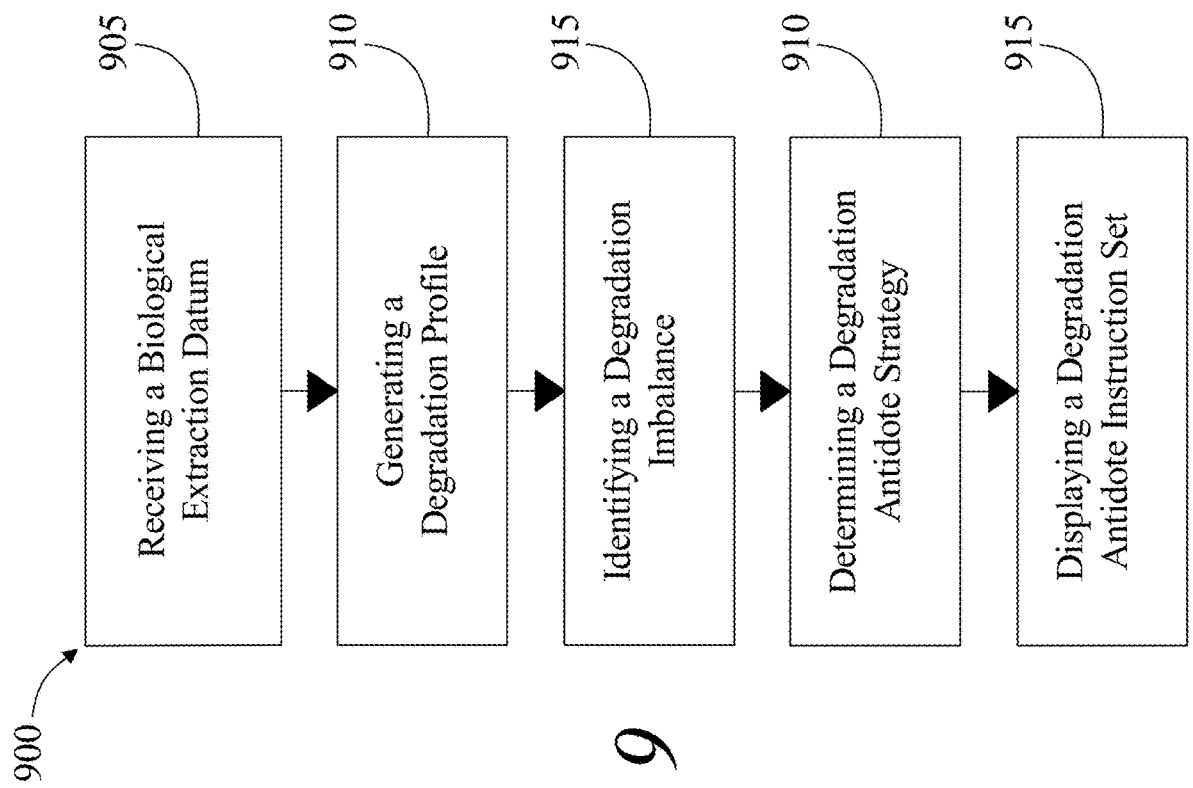
FIG. 9 is a flow diagram illustrating an exemplary method for identifying and ameliorating body degradations.

Referring now to FIG. 9, an exemplary embodiment of a method 900 for identifying and ameliorating body degradations is illustrated. At step 905, computing device 104 may receive a biological extraction datum pertaining to a user; this may be implemented, without limitation, as described above in reference to FIGS. 1-8.

With continued reference to FIG. 9, at step 910, computing device 104 may generate, as a function of a degradation machine-learning model 112 and the biological extraction datum 108, a degradation profile 116, wherein generating the degradation profile 116 may include training the degradation machine-learning model 112 using training data 120 that corresponds to biological extraction data correlated to a threshold value of biological degradation. Computing device 104 may calculate a biological degradation function of a user that is a mathematical function that describes the change in rate of degradation over time corresponding to the degradation data. Generating the degradation profile 116 may include mapping the biological extraction datum 108 to a plurality of mathematical functions that summarize rates of degradation of user physiology; this may be implemented, without limitation, as described above in reference to FIGS. 1-8.

With continued reference to FIG. 9, at step 915, computing device 104 may identify, using a degradation imbalance machine-learning process 132 and the degradation profile 116, a degradation imbalance 136, wherein a degradation imbalance 136 is a rate of biological degradation that exceeds the expected rate of degradation of a threshold value 140. Identifying the degradation imbalance 136 may include determining expected rates of biological degradation using data retrieved from a degradation database 128 and a degradation imbalance machine-learning process 132, wherein the degradation machine-learning process 132 may train standard rate machine-learning model 144 with training data 120 corresponding to normal physiological rates of biological degradation. Computing device 104 may compare the user degradation profile 116 with at least an expected rate of biological degradation, wherein the at least an expected rate of biological degradation is a mathematical function describing the rate of biological degradation over time generated by the standard rate machine-learning model 144. Computing device 104 may calculate a numerical difference between the user degradation profile 116 and the expected rate of biological degradation generated by the standard rate machine-learning model 144; this may be implemented, without limitation, as described above in reference to FIGS. 1-8.

With continued reference to FIG. 9, at step 920, computing device 104 may determine, as a function of the degradation imbalance machine-learning process 132 and the degradation imbalance 136, a degradation antidote strategy 148 to decrease the rate of biological degradation of a user, wherein determining a degradation antidote strategy 148 may include performing a simulation 152, wherein the simulation randomly perturbs a parameter, wherein a parameter is an element of numerical data relating to the at least a user biological extraction datum 108. Computing device 104 may determine which parameters result in the largest decrease in degradation rate. Computing device 104 may match the parameter that results in the largest decrease in degradation rate with a concomitant change in user biological extraction data. Computing device 104 may determine the degradation antidote strategy 148 by retrieving from a database a strategy for reducing the rate of degradation. Computing device 104 performing the simulation 152 may include sampling user biological parameters and performing a simulated degradation function, measuring a change in biological degradation as a function of the simulated degradation function, and determining a parameter aggregate that results in the most decreased degradation rate. Computing device 104 may matching the parameter further comprises using the degradation imbalance machine-learning process to calculate a numerical difference between the simulated aggregate parameters and a current user biological extraction parameter. Determining the degradation antidote strategy 148 may include retrieving, from a degradation database 128, a strategy for addressing a degradation rate, and ranking, as a function of the degradation machine-learning process 132 and a ranking function 156, steps of a degradation antidote strategy. Ranking the steps of a degradation antidote strategy 148 may include generating a logical order of steps, wherein logical relates to the ability of a user to follow the steps in implementing the degradation antidote strategy. Determining a degradation antidote instruction set 160 may include providing the ranked steps of a degradation antidote strategy 148 for a user as a degradation antidote instruction set 160; this may be implemented, without limitation, as described above in reference to FIGS. 1-8.

With continued reference to FIG. 9, at step 925, computing device may display to a user, using the degradation antidote strategy 148 and the degradation machine-learning process 132, a degradation antidote instruction set 160, wherein the instruction set is a logical order of steps for a user to change in user biological extraction data decrease according to the simulation. Computing device 104 may receive updated user data 164, wherein updated user data 164 is user data provided more recent in time than a first degradation antidote instruction set 160 was provided to a user and train the degradation machine-learning model 112 using training data 120 that corresponds to updated user data 164 as it compares to user biological degradation rates. Computing device 104 may calculate, using the degradation machine-learning model 112 trained with updated user data 164, a numerical difference between the user degradation profile 116 and the updated biological degradation rates from the updated user data 164. Computing device 104 may determine if a parameter in the updated biological extraction data 108 resulted in a numerical difference between the updated biological degradation rates and the user biological profile from the degradation antidote instruction set 160.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
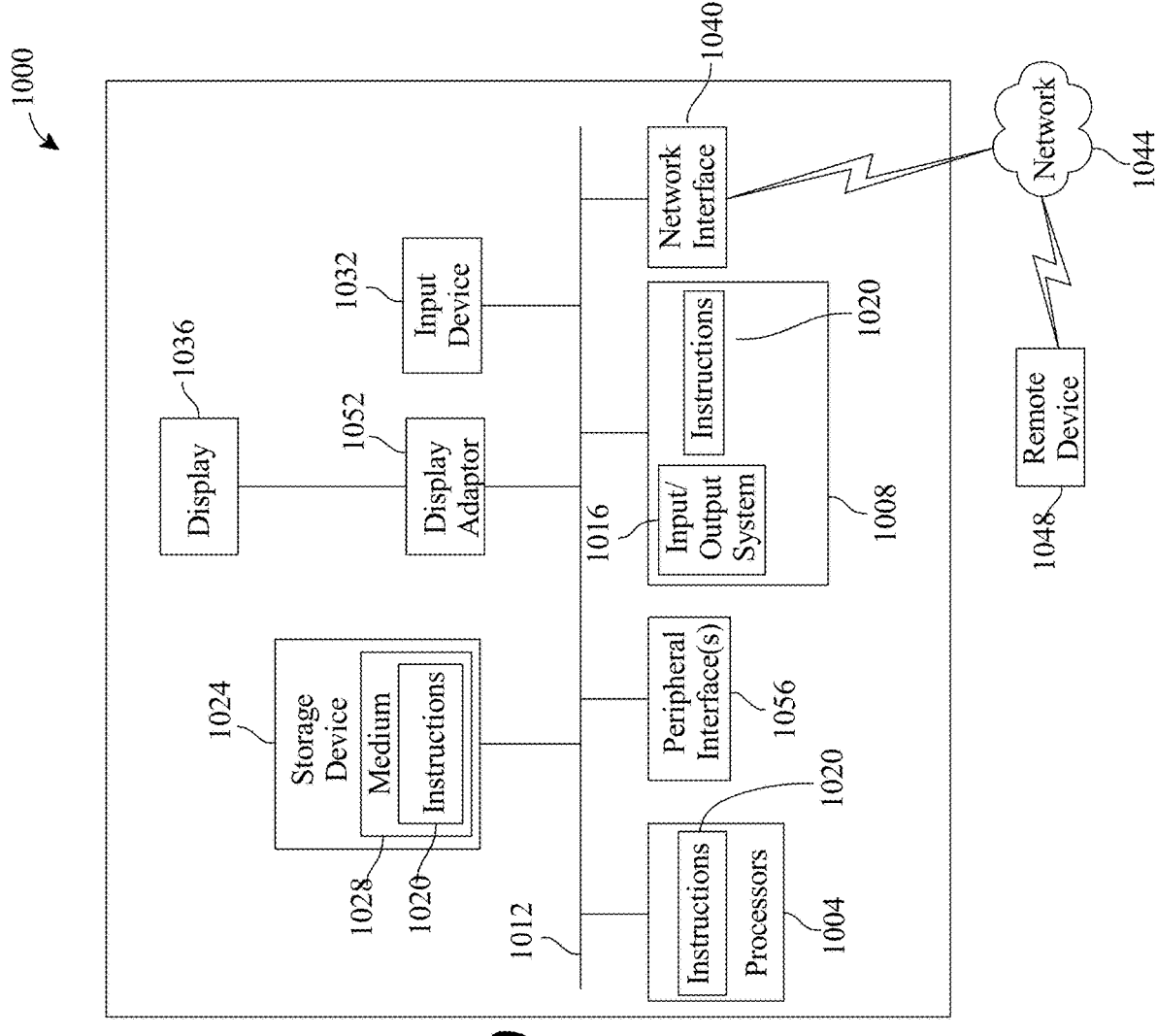
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for identifying and ameliorating body degradations, the system comprising:
    a computing device, wherein the computing device is designed and configured to:
    receive a biological extraction datum pertaining to a user;
    generate a degradation profile including a rate of biological degradation, wherein generating the degradation profile further comprises:
        training a degradation machine-learning model using a training data and a degradation machine-learning process, wherein the training data correlates biological extraction data and biological degradation data; and
        generating the rate of biological degradation as a function of the degradation machine-learning model, wherein the degradation machine-learning model uses the biological extraction datum as an input to output the rate of biological degradation;
    identify, using a rate of biological degradation in the degradation profile, a degradation imbalance, wherein the degradation imbalance is a rate of biological degradation that exceeds a biological degradation rate threshold value, wherein identifying the degradation imbalance further comprises:
        training a standard rate machine-learning model using a training data set and a classifier, wherein training the standard machine-learning model further comprises selecting the training data set as a function of similarity between a physiology of the user and physiologies of other individuals; and
        generating the threshold value as a function of the standard rate machine-learning model, wherein the standard rate machine-learning model uses the physiology of the user as an input to output the biological degradation rate threshold value corresponding to the user;
    determine, as a function of the degradation imbalance, a degradation antidote strategy to decrease the rate of biological degradation of the user, wherein determining the degradation antidote strategy further comprises:
        performing a simulation, wherein the simulation randomly perturbs a parameter, wherein the parameter is an element of numerical data relating to the biological extraction datum;
            wherein performing the simulation further comprises:
            sampling user biological parameters;
            performing a simulated degradation function of the user biological parameters, wherein performing the simulation degradation further comprises using a simulation algorithm to sample the biological parameters using a sampling rate based on a user age and generate a degradation function for each sampled user biological parameter;
            measuring a change in biological degradation as a function of the simulated degradation function; and
            determining a parameter aggregate that results in a maximally decreased degradation rate;
        determining, as a function of the simulation, which parameters result in a maximal degree of decrease in degradation rate using the parameter aggregate;
        generating, as a function of the simulation, a degradation curve for the parameters that result in the maximum degree of decrease in the degradation; and
        determining the degradation antidote strategy as a function of the parameters that result in the maximal degree of decrease in the degradation rate and the degradation curve; and
    display to the user, as a function of the degradation antidote strategy and a ranking process, a degradation antidote instruction set.

2. The system of claim 1, wherein identifying the degradation imbalance further comprises:
    calculating a numerical difference between the biological degradation rate threshold value generated by the standard rate machine-learning model with the biological degradation rate in the degradation profile, and
    determining if the numerical difference between the biological degradation rate threshold value and the rate of biological degradation of the user correlates to a degradation imbalance.

3. The system of claim 2, wherein the standard rate machine-learning model is trained using the classifier which classifies user physiology data to the training data set.

4. The system of claim 1, wherein determining the degradation antidote strategy further comprises retrieving from a database at least a strategy for reducing the rate of degradation as a function of the parameters that result in the maximal degree of decrease in the degradation rate.

5. The system of claim 4, wherein the computing device is further configured to:
    calculate an effect of the at least a strategy on the degradation imbalance, wherein calculating an effect includes determining a numerical value that described the impact of the strategy on the degradation imbalance; and
    select the degradation antidote strategy based on the calculated impact.

6. The system of claim 1, wherein performing the simulation further comprises:
    sampling user biological parameters;
    performing a simulated degradation function of the user biological parameters, wherein performing the simulation degradation further comprises using a simulation algorithm to sample the biological parameters and generate a degradation function for each sampled user biological parameter;

measuring a change in biological degradation as a function of the simulated degradation function; and determining a parameter aggregate that results in a maximally decreased degradation rate.

7. The system of claim 1, wherein determining further comprises calculating a numerical difference between the simulation parameter output and the current user biological extraction datum.

8. The system of claim 1, wherein determining the degradation antidote strategy further comprises:

ranking, using a ranking function, steps of the degradation antidote strategy, wherein ranking further comprises weighting the steps based on at least a criterion; and generating a logical order of steps of the degradation antidote strategy for the user to follow.

9. The system of claim 1, wherein determining the degradation antidote instruction set further comprises providing ranked steps of the degradation antidote strategy for the user as the degradation antidote instruction set to a user device operated by the user.

10. The system of claim 1, wherein the computing device is designed and configured to:

receive updated user data, wherein updated user data is user data provided more recent in time than a first degradation antidote instruction set was provided to the user;

calculate, using the degradation machine-learning model and the updated user data, a numerical difference between the degradation profile and at least an updated biological degradation rate from the updated user data; and determine if a parameter in the updated user data resulting in a numerical difference between the at least an updated biological degradation rate and the degradation profile resulted from the degradation antidote instruction set.

11. A method for identifying and ameliorating body degradations, the method comprising:

receiving, by a computing device, a biological extraction datum pertaining to a user;

generating, by the computing device, a degradation profile including a rate of biological degradation, wherein generating the degradation profile further comprises:

training a degradation machine-learning model using a training data and a degradation machine-learning process, wherein the training data correlates biological extraction data and biological degradation data; and generating the rate of biological degradation as a function of the degradation machine-learning model, wherein the degradation machine-learning model uses the biological extraction datum as an input to output the rate of biological degradation;

identifying, by the computing device, using the rate of biological degradation in the degradation profile, a degradation imbalance, wherein the degradation imbalance is a rate of biological degradation that exceeds a biological degradation rate threshold value, wherein identifying the degradation imbalance further comprises:

training a standard rate machine-learning model using a training data set and a classifier, wherein training the standard machine-learning model further comprises selecting the training data set as a function of similarity between a physiology of the user and physiologies of other individuals; and generating the threshold value as a function of the standard rate machine-learning model, wherein the standard rate machine-learning model uses the physiology of the user as an input to output the biological degradation rate threshold value corresponding to the user;

determining, by the computing device, as a function of the degradation imbalance, a degradation antidote strategy to decrease the rate of biological degradation of the user, wherein determining the degradation antidote strategy further comprises:

performing a simulation, wherein the simulation randomly perturbs a parameter, wherein the parameter is an element of numerical data relating to the biological extraction datum;

wherein performing the simulation further comprises:

sampling user biological parameters;

performing a simulated degradation function of the user biological parameters, wherein performing the simulation degradation further comprises using a simulation algorithm to sample the biological parameters using a sampling rate based on a user age and generate a degradation function for each sampled user biological parameter;

measuring a change in biological degradation as a function of the simulated degradation function; and determining a parameter aggregate that results in a maximally decreased degradation rate;

determining, as a function of the simulation, which parameters result in a maximal degree of decrease in degradation rate using the parameter aggregate;

determining, as a function of the simulation, which parameters result in a maximal decrease in degradation rate;

generating, as a function of the simulation, a degradation curve for the parameters that result in the maximum degree of decrease in the degradation; and determining the degradation antidote strategy as a function of the parameters that result in the maximal degree of decrease in the degradation rate and the degradation curve; and displaying to the user, by the computing device, as a function of the degradation antidote strategy and a ranking process, a degradation antidote instruction set.

12. The method of claim 11, wherein identifying the degradation imbalance further comprises:

calculating a numerical difference between the biological degradation rate threshold value generated by the standard rate machine-learning model with the biological degradation rate in the degradation profile; and determining if the numerical difference between the biological degradation rate threshold value and the rate of biological degradation of the user correlates to a degradation imbalance.

13. The method of claim 12, wherein the standard rate machine-learning model is trained using the classifier which classifies user physiology data to the training data set.

14. The method of claim 11, wherein determining the degradation antidote strategy further comprises retrieving from a database at least a strategy for reducing the rate of degradation as a function of the parameters that result in the maximal degree of decrease in the degradation rate.

15. The method of claim 14, wherein retrieving the at least a strategy further comprises:
- calculating an effect of the at least a strategy on the degradation imbalance, wherein calculating an effect includes determining a numerical value that described the impact of the strategy on the degradation imbalance; and
- selecting the degradation antidote strategy based on the calculated impact.

16. The method of claim 11, wherein performing the simulation further comprises:
- sampling user biological parameters;
- performing a simulated degradation function of the user biological parameters, wherein performing a simulation further comprises using a simulation algorithm to sample the biological parameters and generate a degradation function for each sampled parameter;
- measuring a change in biological degradation as a function of the simulated degradation function; and
- determining a parameter aggregate that results in a maximally decreased degradation rate.

17. The method of claim 11, wherein determining further comprises calculating a numerical difference between the simulation parameter output and the current user biological extraction data.

18. The method of claim 11, wherein determining the degradation antidote strategy further comprises:
- ranking, using a ranking function, steps of the degradation antidote strategy, wherein ranking further comprises weighting the steps based on at least a criterion; and
- generating a logical order of steps of the degradation antidote strategy for the user to follow.

19. The method of claim 11, wherein determining the degradation antidote instruction set further comprises providing ranked steps of a degradation antidote strategy for the user as the degradation antidote instruction set to a user device operated by the user.

20. The method of claim 11 further comprising:
- receiving updated user data, wherein updated user data is user data provided more recent in time than a first degradation antidote instruction set was provided to the user;
- calculating, using the degradation machine-learning model and the updated user data, a numerical difference between the degradation profile and at least an updated biological degradation rate from the updated user data; and
- determining if a parameter in the updated user data resulting in a numerical difference between the at least an updated biological degradation rate and the degradation profile resulted from the degradation antidote instruction set.

* * * * *